(12) United States Patent
Rosentreter et al.

(10) Patent No.: US 7,186,379 B2
(45) Date of Patent: Mar. 6, 2007

(54) CONTINUOUS REAL-TIME MEASUREMENT OF AQUEOUS CYANIDE

(75) Inventors: Jeffrey J. Rosentreter, Pocatello, ID (US); Kevin L. Gering, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 723 days.

(21) Appl. No.: 10/071,017

(22) Filed: Feb. 7, 2002

(65) Prior Publication Data

US 2002/0151082 A1    Oct. 17, 2002

Related U.S. Application Data

(60) Provisional application No. 60/267,291, filed on Feb. 7, 2001.

(51) Int. Cl.
- *B32B 5/02* (2006.01)
- *B32B 27/04* (2006.01)
- *B32B 27/12* (2006.01)
- *G01N 15/06* (2006.01)
- *G01N 35/00* (2006.01)

(52) U.S. Cl. ............... 422/82.01; 422/50; 422/62; 422/63; 422/68.1; 422/81; 422/82; 436/43; 436/52; 436/106; 436/109; 436/174; 436/175; 436/177; 436/178; 73/1.01; 73/1.02; 73/53.01; 73/1.82

(58) Field of Classification Search ............ 422/50, 422/62, 63, 68.1, 81, 82, 82.01; 436/43, 436/52, 106, 109, 174, 175, 177, 178; 73/1.01, 73/1.02, 53.01, 1.82

See application file for complete search history.

(56) References Cited

U.S. PATENT DOCUMENTS

| | | | | |
|---|---|---|---|---|
| 4,713,618 A | * | 12/1987 | Carlson et al. | 324/438 |
| 4,735,906 A | * | 4/1988 | Bastiaans | 436/527 |
| 4,808,538 A | * | 2/1989 | Roffey et al. | 436/6 |
| 4,844,611 A | * | 7/1989 | Imahashi et al. | 356/246 |
| 5,235,238 A | * | 8/1993 | Nomura et al. | 310/349 |
| 5,365,559 A | * | 11/1994 | Hsueh et al. | 377/10 |
| 6,196,059 B1 | * | 3/2001 | Kosslinger et al. | 73/61.49 |

OTHER PUBLICATIONS

M. R. Deakin and D. A. Buttry, "Electrochemical Applications of the Quartz Brystal Microbalance", Anal. Chem., 61 (1989) 1147A.
A. G. Sharpe, *The Chemistry of Cyano Complexes of Transition Metals*, (London Academic Press, 0976).
G. Sauerbrey, Z. *Physik*, 155. (1959) 206.
US EPA, "Methods for Chemical Analysis of Water and Wastes", EPA-600/7-79-020 (1979).

(Continued)

*Primary Examiner*—Brian Sines
(74) *Attorney, Agent, or Firm*—Alan D. Kirsch

(57) ABSTRACT

This invention provides a method and system capable of the continuous, real-time measurement of low concentrations of aqueous free cyanide (CN) using an on-line, flow through system. The system is based on the selective reactivity of cyanide anions and the characteristically nonreactive nature of metallic gold films, wherein this selective reactivity is exploited as an indirect measurement for aqueous cyanide. In the present invention the dissolution of gold, due to the solubilization reaction with the analyte cyanide anion, is monitored using a piezoelectric microbalance contained within a flow cell.

30 Claims, 5 Drawing Sheets

OTHER PUBLICATIONS

C. R. Parker, "Water Analysis by Atomic Absorption Spectroscopy" (Varian Techtron: Palo Alto, California, 1972).

L. Wilson, *Anal. Chim. Acta.*, 30, (1964) 377.

H. Boltz, *Colorimetric Determination of Nonmetals in Chemical Analysis,* vol. 8; 1979) 78-81.

T. Pal, A. Granguly, and D. Maity, *Anal. Chem,* 58, (1986) 1564-1566.

Hach Chemical Company, "Cyanide/Iodide Electrode Model 44410 Manual", (Loveland, Colorado.: Hach Chemical Company).

* cited by examiner

CONTINUOUS REAL-TIME MEASUREMENT OF AQUEOUS CYANIDE

This application claims the benefit of U.S. Provisional Application No. 60/267,291 for Novel-Detector for Real-Time Measurement of Aqueous Cyanide filed Feb. 7, 2001, which is hereby incorporated by reference.

CONTRACTUAL ORIGIN OF THE INVENTION

This invention was made with United States Government support under Contract No. DE-AC07-94ID13223, now Contract No. DE-AC07-99ID13727 awarded by the United States Department of Energy. The United States Government has certain rights in the invention.

BACKGROUND OF THE INVENTION

This invention relates to a method and system for the real-time measurement of aqueous cyanide and more particularly to method and system for the continuous, real-time measurement of cyanide using a quartz crystal microbalance (QCM).

There are numerous industrial processes that would benefit from a continuous on-line cyanide detection device that serves as a means for monitoring process performance and environmental compliance (i.e., downstream discharge levels). Such a device would find immediate applicability in leach-mining operations, electroplating facilities, hydrocarbon refining and chemical synthesis plants, environmental monitoring, and others.

The present invention overcomes many of the shortcomings experienced by conventional cyanide measurement techniques, as described below. The methods and procedures for conventional cyanide analytical methods suffer from two primary types of inadequacies. The first problem is the inability to obtain reliable results at concentrations low enough to be meaningful, i.e. the detection limit problem. This is a crucial issue since the detection limits for accepted methods of cyanide analysis often exceed or barely meet the EPA-defined cyanide level of 5 µg/L for freshwater and marine aquatic life.

The second area of inadequacy stems from the fact that a wide variety of chemical compounds commonly associated with natural waters and cyanide solutions can cause chemical interferences for the detection methods. Such chemical interferences can compromise accurate cyanide quantification and have a detrimental effect on a method's precision in determining detection limits. Both of these problems are significant barriers to the accurate monitoring of cyanides in mining processes.

Currently the difficulties tied to analytical detection limits for accepted methods are such that the EPA has set a regulation that cannot be rigorously and reliably attained. This places all those wishing to comply with the regulation in a "Catch-22" situation. In examining the detection methods we find that the titrimetric method has the highest limit of detection. The ASTM Procedure indicates that a skilled and experienced analyst can obtain reliable cyanide determinations at concentrations down to 1000 µg/L. This is nearly three orders of magnitude above the maximum allowable concentration of cyanide. The colorimetric and potentiometric methods provide significantly better sensitivity. The calorimetric method has been used to provide the bulk of the currently available environmental cyanide data. Utilizing guidelines provided by the EPA, the colorimetric method provides a detection limit of 20 µg/L, which is four times higher than the EPA limit, and this is only within a 10 percent error. The potentiometric determination technique has a lower limit of detection of approximately 26 µg/L, still five times that of the maximum allowable cyanide concentration. This leaves only the automated UV method, which in its procedure has stated a method limit of detection of 5 µg/L. This means a sample containing the maximum allowable concentration of cyanide produces a signal that is just discernable. Unfortunately, thiocyanate ($SCN^-$) is also detected by this method and since very few cyanide samples exist without thiocyanate also present, and since there is no reliable method that determines thiocyanate without cyanide interfering, the UV method detection limit is also uncertain. To complicate these analyses further, each of these methods has a wide variety of other possible interferences, making the stated problems with detection limits somewhat ubiquitous among current methods.

Of the many chemical species that interfere with the cyanide detection methods, thiocyanate is by far the most serious. This is due in part to the fact that thiocyanate is often present in a large excess relative to the cyanide content of a sample. This is especially true for solutions produced by the mining industry, where cyanide quickly reacts with sulfides in the ore during the cyanidation process.

The same reaction occurs in natural waters containing sulfide and in the alkaline absorbers used in the distillation methods. During distillation, hydrogen sulfide distills with the newly created free cyanide and both are absorbed in the scrubber solution. Here, the cyanide, which was present as a complex, now freely reacts with the sulfide. This reaction is accelerated at elevated temperatures and pH, which are precisely the conditions present in the scrubber solution. This is a significant problem since thiocyanate reacts equally well as cyanide to chloramine-T, therefore allowing both ions to be colorized in the colorimetric procedure, making thiocyanate a major positive interference for the most widely used cyanide determination method. Potentiometric detectors are also affected by the thiocyanate ion. Utilizing some of the newest cyanide ion selective electrodes available, it is reported that a one hundred-fold excess of thiocyanate produces a positive interference equivalent to nearly three times the equivalent amount of cyanide present. Sulfide has also been shown to deactivate the surface of the cyanide electrodes when they are immersed in sulfide containing solutions. While this interference-deactivation translates to only a minor interference for distilled samples, it precludes the direct use of the ion selective electrode in natural water samples.

Thiocyanate is almost completely decomposed during the UV-digestion used in the automated analysis, leading to a large positive interference. The UV-digestion procedures require a separate analysis for thiocyanate, if present, in order to correct the total cyanide value. The methods of analysis commonly used for the determination of thiocyanate are colorimetric and are the same methods which are used for cyanide, the pyridine-pyralozone method and the copper-pyridine method. Therefore, cyanides are a serious interference in both methods. This illustrates that while the automated UV-digestion method reports the lowest detection limits among the currently accepted cyanide detection methods, the use of this method is severely limited by the thiocyanate interference. In summary, the thiocyanate ion is the root of much discourse in cyanide analyses, since it (a) interferes with all sensitive cyanide detection techniques, and (b) itself is not easily measured or completely maskable making the corrections for thiocyanate unreliable.

In a marked deviation from the standard methods of cyanide determinations, the piezoelectric detection method and system of the present invention is largely free from chemical interferences. It is seen that detector sensitivity is practically independent of the presence of common cations and anions. Perhaps the most important result shown in FIG. 6 is that thiocyanate interference is also extremely minimal, yet quantitative. As a result thiocyanate generally produces no performance limiting interference for QCM operation.

An advantage of the present invention is that it can provide continuous analysis, whereas the other methods require longer analysis times. This advantage provides for near-immediate process control for systems requiring adjustments related to a changing cyanide level (e.g., leach mining operations involving cyanide). Tighter process controls allow for a more economical use of chemicals and materials consumed by a given system.

It is therefore an object of this invention to provide a continuous, real-time aqueous cyanide detection method and system at very low detection levels (e.g., down to 1 µg/L) that is largely free from chemical interferences.

It is another object of this invention to provide a cyanide detection method and system that is essentially independent of the presence of cations and anions.

It is still another purpose of this invention to provide a cyanide detection method and system to quantify and minimize thiocyanate interference.

Additional objects, advantages and novel features of the invention will become apparent to those skilled in the art upon examination of the following and by practice of the invention.

SUMMARY OF THE INVENTION

To achieve the foregoing and other objects, the present invention provides a method and system capable of the continuous, real-time measurement of trace concentrations of aqueous free cyanide ($CN^-$) using an on-line, flow through system. The method and system of the present invention is based on the selective reactivity of cyanide anions and the characteristically nonreactive nature of metallic gold films, wherein this selective reactivity is exploited as an indirect measurement for aqueous cyanide.

In one embodiment of the invention, a method for the real-time measurement of aqueous cyanide is provided, comprising: providing a cyanide laden water test specimen in a flow cell, said flow cell adapted to contain a gold-plated piezoelectric crystal having a surface in fluid communication with said test specimen; providing a controller to control the oscillation frequency of piezoelectric crystal; determining the cyanide concentration within said test specimen by measuring a change in said crystal oscillation frequency caused by a chemical reaction between free cyanide and the gold-plated piezoelectric crystal.

In another embodiment of the invention, a system for continuous, real time cyanide concentration measurement system is provided, comprising; at least one flow cell adapted to contain a gold-plated piezoelectric crystal, said crystal having first and second surfaces, said first surface configured to contact a test specimen within the at least one flow cell and said second surface configured to contact an ambient atmosphere; a controller to control and measure changes in oscillation frequency of said crystal caused by a chemical reaction between free cyanide within the test specimen and the gold-plated piezoelectric crystal.

The system is capable of continuous operation through the use of dual piezoelectric oscillator circuits so that multiple flow cells, each containing piezoelectric crystals, can be used for simultaneous cyanide concentration measurements.

BRIEF DESCRIPTION OF THE DRAWINGS

The present invention is illustrated in the accompanying drawings where.

DETAILED DESCRIPTION OF THE INVENTION

Figure 1:
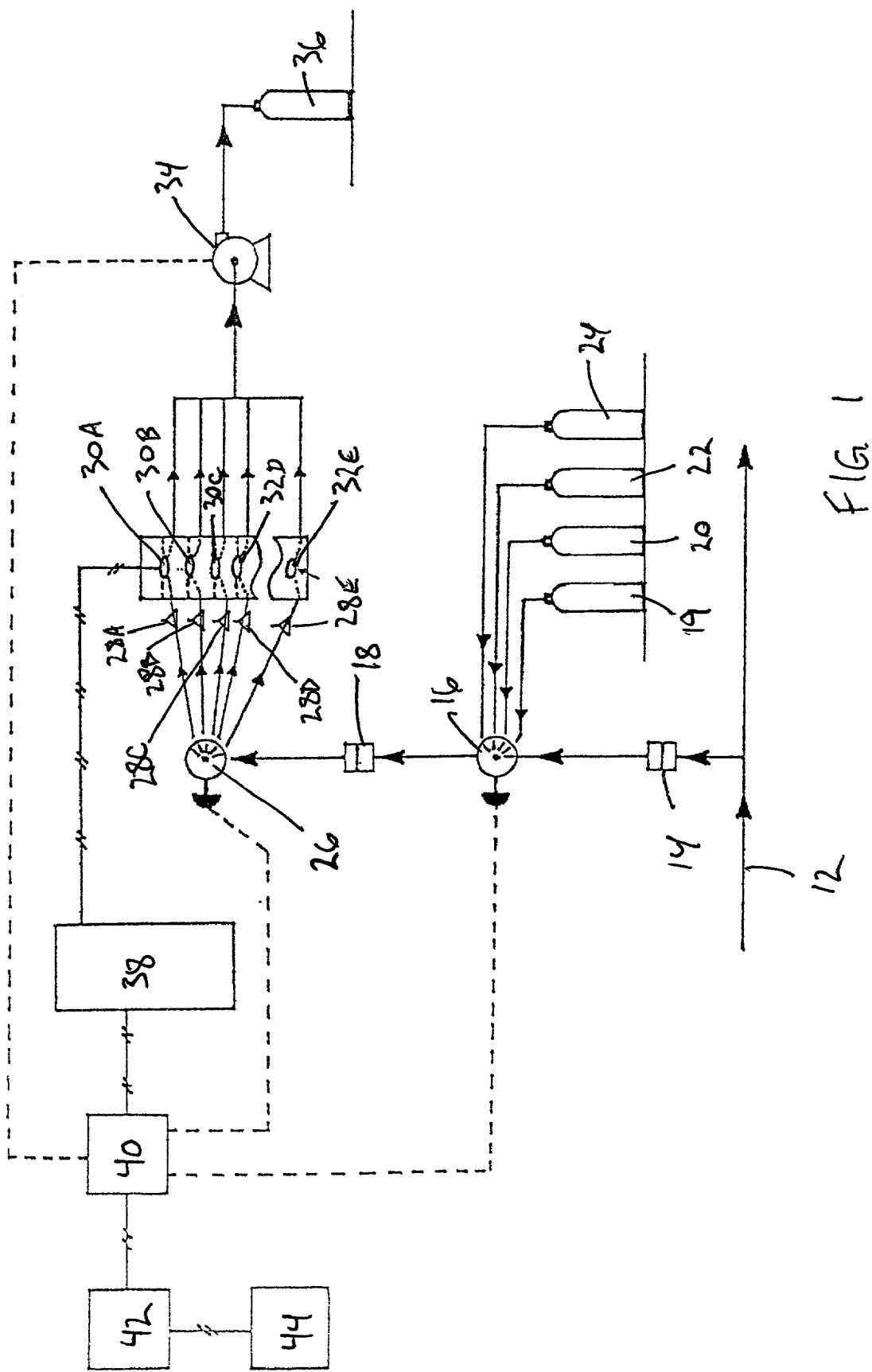
FIG. 1 is a schematic diagram of the present invention.
Figure 2:
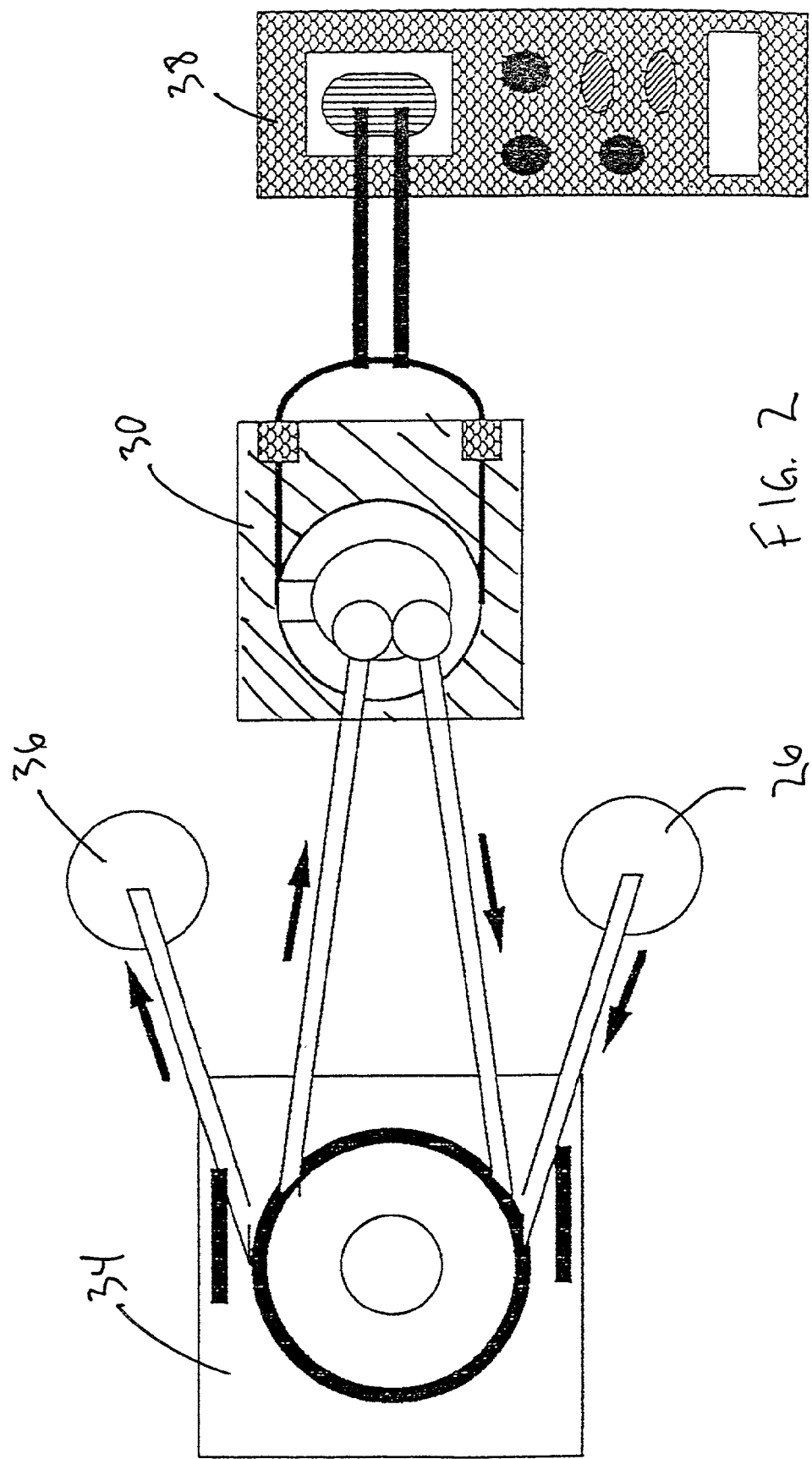
FIG. 2 is simplified schematic diagram of the present invention showing the flow cell in a sectional view.

Referring now to the drawings in which like numerals represent like elements throughout the several views, the preferred embodiment of the present invention will be described.

This invention provides a method and apparatus capable of the continuous, real-time measurement of trace concentrations of aqueous free cyanide ($CN^-$) using an on-line, flow through system. For purposes of this application, real time measurement is considered the capability to obtain cyanide measurements with a precalibrated piezoelectric crystal immediately following a short equilibration period (typically as short as 2 minutes) of the sample within the flow cell. Equilibration periods may vary between samples, and can be reduced by providing a means of mixing the flow cell contents through one the techniques describe hereinafter.

The system is based on the selective reactivity of cyanide anions and the characteristically nonreactive nature of metallic gold films, wherein this selective reactivity is exploited as an indirect measurement for aqueous cyanide. In the present invention the dissolution of gold, due to the solubilization reaction with the analyte cyanide anion, is monitored using a piezoelectric microbalance contained within a flow cell.

In the case of the cyanide detector the quartz crystal is partially coated with gold, wherein the reaction stoichiometry is given by the Elsner reaction $$4Au^\circ + 8CN^- + 2H_2O + O_2 \rightarrow 4Au(CN)_2^- + 4OH^-$$ Eq. 1

The result of Equation 1 is dissolution of gold. For the present invention the source of elemental gold is gold plating that sandwiches a piezoelectric quartz crystal. Due to the orientation of the piezoelectric crystal in a dynamic flow chamber, the reacted gold is effectively removed from the crystal. This mass loss of gold is detected by the piezoelectric effect of the AT-cut quartz crystal through a change in vibrational frequency. The relationship between the mass loss of gold and the corresponding change in harmonic oscillating frequency is given by the Suaerbrey equation, where the mass sensitivity of a piezoelectric crystal is related to its fundamental frequency according to:

$$\Delta F = -2.3 \times 10^{6} * F^2 \Delta M / A$$ Eq. 2 where ΔF=change in frequency, Hz;
F=fundamental frequency of crystal, MHz;
ΔM=change in mass, g; and
A=area of quartz electrode, $cm^2$.

FIG. 1 represents the schematic diagram of the cyanide detection system 10 of the present invention. The process description is as follows. Cyanide-laden water 12 is pumped through an in-line filter 14 and is directed through a switching valve 16 according to the sequence of the sampling protocol (see FIG. 3). The cyanide-laden water 12 then passes through an optional second filter 18 which is installed to remove potential impurities from the standard solutions comprising distilled/deionized water 19, standard high concentration $CN^-$ solution 20, standard middle concentration $CN^-$ solution 22 and standard low concentration $CN^-$ solution 24. Standard solutions are bracketed with concentrations to encompass the anticipated range of sample concentrations, and would typically range from 1 to 1000 μg/L cyanide. The standard concentrations, which can be any number of different concentrations, are used to calibrate the system. The cyanide laden water 12, or alternatively the standard concentration solutions (20, 22 or 24) then passes through a second switching valve 26 where it is directed through a bubble eliminator (shown in FIG. 1 as 28A, 28B, 28C, 28D, and 28E) to the currently active quartz crystal within the flow cell stack 30. Alternately, a single bubble eliminator could be placed just prior to switching valve 26.

The sample preconditioning steps of filtration and bubble elimination can also be conducted in a single front-end device. The quality of the incoming raw sample liquid will dictate the mode of filtration and the type of filtration medium. For example, samples containing very low levels of suspended solids could make use of disposable filters (e.g., a filtration disk cartridge or a syringe filter) adding a level of simplicity and economy to the system's operation. However, a permanent, back-washable filter should be used for incoming samples having high solids content (such as those from an ore slurry); benefits in this case would arise from avoiding the cost of numerous disposable filters and from eliminating the time required of operators to change out clogged disposable filters.

Depending upon the characteristics of the sample stream, pH adjustment and the removal of interfering metals may be required preconditioning steps. The pH stability would be monitored and adjusted as needed base on sensitivity requirements using in-line water splitting techniques to create hydroxide or hydronium ions as needed to increase or decrease sample pH, respectively. Preferably the pH is between 10 and 12. Reducible metals should be removed to avoid electroplating these interfering ions onto the reactive gold electrodes. These metals can be effectively removed by using selective membrane filtration (e.g., ion selective membranes). For example, the membrane could be used to selectively allow the passage of free cyanide through the membrane to the surface of the piezoelectric quartz crystal, whereas detrimental chemical species would be rejected at the membrane surface. Such chemical species would be those that either precipitate or absorb onto the piezoelectric quartz crystal surface or compete for the gold coating on the piezoelectric quartz crystal. For example, certain mono and divalent metals (e.g., Fe, Cu, and Ni) could precipitate onto the piezoelectric quartz crystal surface under conditions favorable to oxidation-reductions reactions. Thus, improved accuracy of the piezoelectric response and increased electrode lifetime would be gained by the use of a selectively permeable membrane to precondition the incoming sample.

The flow cell stack contains multiple gold-plated piezoelectric crystals (Shown in FIG. 1 as 32A, 32B, 32C, 32D, and 32E), where the crystals are used singly until the useful lifetime of each has been exhausted by excessive loss of gold mass, as evident by erratic piezoelectric response. The flow cell stack 30 should be expandable to allow for as many crystals to be installed as required for a particular application. Upon leaving the flow cell stack 30 the cyanide water 12 is pumped via pump 34 to a small vessel 36 that will hold the spent analyte for later gold recovery.

The piezoelectric oscillator/frequency counter 38 records the vibrational frequency of the active quartz crystal and forwards the information to the control box 40. Using programmed logic, the control box 40 determines the operational parameters of the detection system based on the sampling protocol, date/time, and crystal vibration frequency stability (gold electrode degradation) and performs the necessary calculations to convert vibrational frequency data into cyanide concentration data (See Equations 1 and 2).

Additionally, dual piezoelectric (oscillator) circuits can be used in the present invention to allow more that one sample to be analyzed for cyanide at a time. The dual circuits would operated at the same or dissimilar frequencies. The operational benefit from having dual piezoelectric oscillator circuits is to have the circuits operate at or near the same frequency, wherein (1) a piezoelectric quartz electrode connected to one circuit would facilitate sample analysis, while (2) the other circuit would be in connection with another electrode that is undergoing calibration via standard solutions in preparation of sample analysis. Thus each electrode would alternately perform sample analysis and calibration so that there is always one electrode engaged in sample analysis.

The control box 40 actuates the first switching valve 16 (directing the appropriate solution downstream toward the flow cell stack), the second switching valve 26 (directing the solution into the appropriate flow cell), and the pump 34 (running the pump for the prescribed time for each leg of the sampling protocol). Pump 34 can be any type of pump capable of transporting the water specimen to be tested, such as a peristaltic pump, electromagnetic pump or other electrical pumps. Pump 34 can alternately be placed between switching valve 16 and in-line filter 18.

In one embodiment of the invention, the flow cell(s) that house the piezoelectric crystal(s) is modified to allow for quicker equilibration of the standard solutions and sample liquids by promoting thorough mixing of the flow cell contents. This embodiment results in more "real-time" operation by reducing the amount of time required per cyanide analysis through diminishing diffusion-limited processes within the flow cell. This embodiment can be used singly or in combination to achieve this improvement in performance. The following techniques can be used to achieve this improved performance. First, ultrasonic vibration of flow cell contents would promote mixing within the flow cell and decrease equilibration delays that are due to mass-transfer diffusion limitations. This is accomplished through using alternating operation of sample mixing/agitation and measurement. For example, one scenario would be to incorporate a repeated cycle of a 2-second ultrasonic burst followed by a 5-second vibrational monitoring of the piezoelectric crystal. The liquid sample is considered sufficiently equilibrated when successive cycles of piezoelectric operation show a near-zero alteration in quartz crystal vibrational frequency.

Another technique to reduce the analysis time in the present invention is through the use of a micro-stirrer integrated with the flow cell to increase mixing within the flow cell and decrease equilibration delays that are due to mass-transfer limitations. This can be achieved by altering the flow cell internal structure to incorporate a micro stir bar or blade, which would be controlled by a micro magnetic stirrer external to the flow cell. Alternately, a gear-driven micro propeller blade could be integrated into the flow cell, wherein the well-sealed propeller shaft would be operated by a small electric motor outside the flow cell. Concurrent or sequential operation of the stirrer in relation to the piezoelectric crystal vibration is achieved as discussed above for ultrasonic vibration.

Cyanide concentration versus time data is passed from the control box 40 to an output device 42, such as a pen plotter, a liquid crystal or other visual display. Finally, the ([CN$^-$], time) data is sent to a digital data storage device 44 which could be periodically downloaded onto a central computer, or transferred to a central receiving device via radio transmission.

EXPERIMENTAL STUDIES

The equipment used to perform cyanide measurement includes a commercial microprocessor-controlled piezoelectric oscillator and frequency counter, a single flow cell containing a gold-plated quartz crystal, and a peristaltic pump. These components can be used with little or no modifications in the advanced detection system described above and shown in FIG. 1. The piezoelectric oscillator and frequency counter is a Universal Sensors model PZ-105 Piezoelectric Detector, a dual crystal system with single reference and analytical crystals. The oscillator operates 5 to 15 MHz crystals while frequency differences range from −32768 to +32768 Hz. Our application incorporates 10 MHz, AT-cut quartz crystals (with gold electrodes) between 5 and 6 mm diameter; these crystals were chosen due to their availability and high mass sensitivity. The crystals are mounted in a 40 micro liter integrated flow cell, designed for a 9 to 10 MHz crystal. The two piece flow cell is made of acrylic and held together by nylon thumb screws. The oscillator, crystals and flow cell are available from Universal Sensors, Inc. (New Orleans, La.). Finally, solutions are pumped throughout the flow cell using a peristaltic pump (Rainin Instrument model Gilmore M312). Pump tubing of various sizes are used to obtain flow rates of 0.10 mL/min to 0.41 mL/min.

Figure 4:
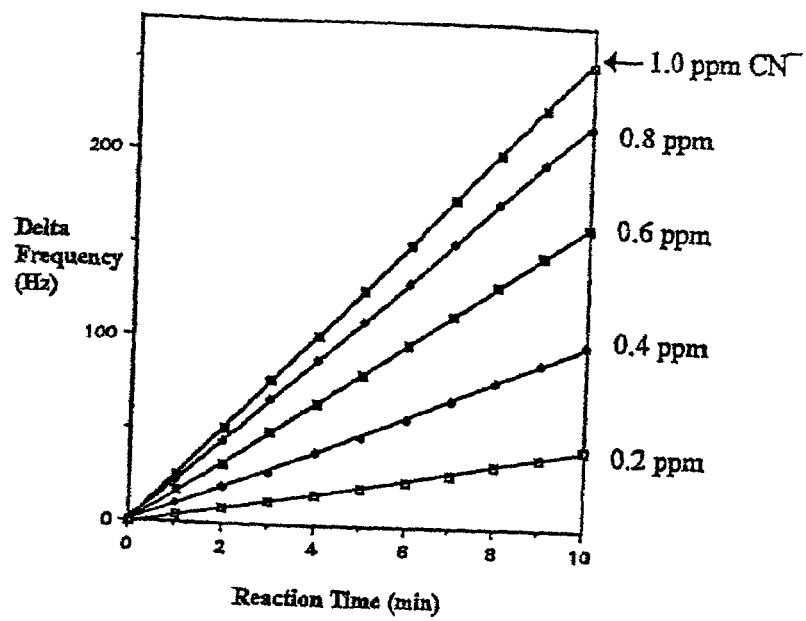
FIG. 4 is a chart showing the oscillation frequency change for cyanide solutions of various concentrations.
Figure 5:
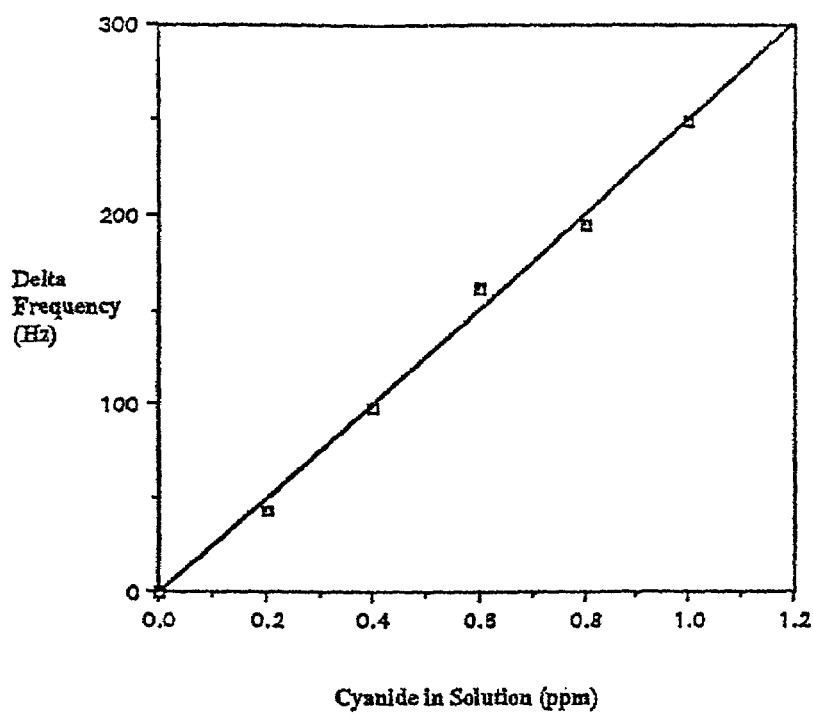
FIG. 5 is a chart showing a single detection time interval of a cyanide measurement.
Figure 6:
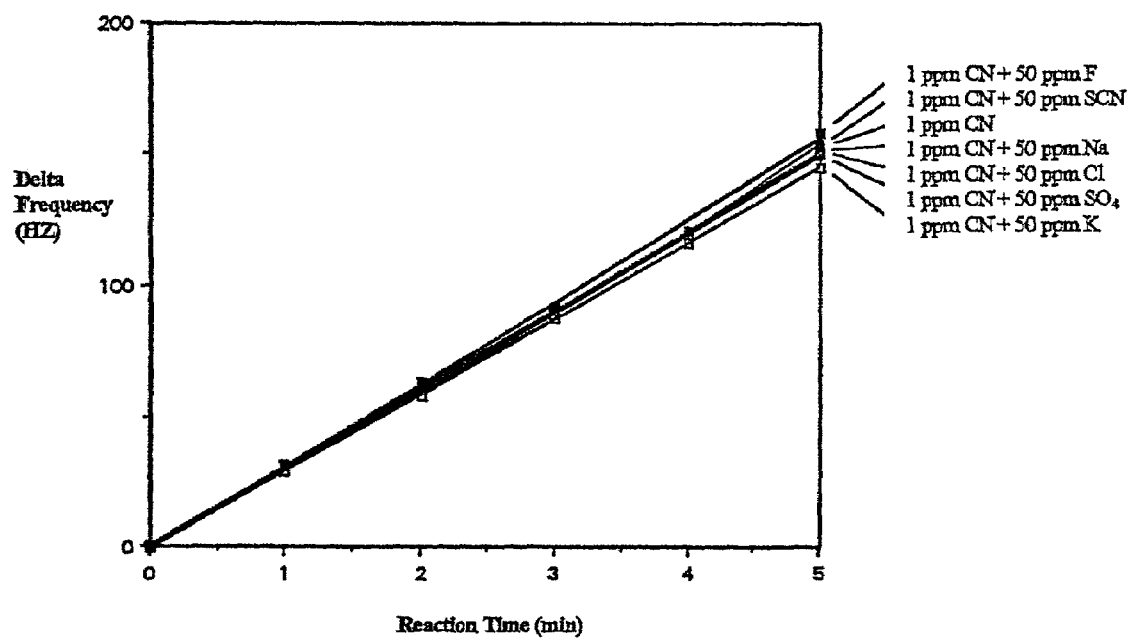
FIG. 6 is a chart illustrating the minimal quantitative impact of chemical interferences.

The laboratory prototype of the present invention can measure cyanide within the wide range of 5 micrograms per liter to 100 milligrams per liter, a range that captures many applications without the need for sample dilution. Sample dilution may be desirable, however, to extend the lifetime of the quartz crystal microbalance electrode, since the longevity and stability of the quartz electrode depends on the integrity of the gold coating. The time required for analysis is as short as 2 minutes per measurement, which accounts for the time required for crystal equilibration. Sample size per measurement depends on the volume of the detector flow cell, but is typically less than a few ml. This small sample requirement minimizes the waste volume produced from spent samples. Standard solutions of cyanide are used periodically to calibrate the detector. FIG. 4 provides typical response data for the detection of cyanide solutions of various concentrations. Here continuous monitoring provides ΔHz slope data for improved sensitivity. Typically the data is simplified by choosing a single detection time interval as seen in FIG. 5, where the cyanide concentrations are directly related to the observed frequency variations after ten minutes equilibration time. It should be noted from FIG. 4 that the linear response at lower time values indicates that reliable cyanide measurements can be made at time values much less than ten minutes.

Integrity of the piezoelectric crystal surface can be enhanced by preparing the gold-plated piezoelectric crystals with a fluorinated spray coating (such as Teflon(g) obtained from a commercial spray coating (Scotchgard®, 3M). This preparation is done by placing a drop (e.g. 30 μL) of deionized water on the center of the gold electrode to act as a mask, then spraying the uncovered portion of the electrode with Teflon. After several minutes the electrode is washed and air dried. This process is repeated for the other side of the electrode and the electrode is allowed to air dry before it is used. The quartz crystal is mounted in the liquid flow cell so as to expose one side of the crystal to the 40 μL liquid chamber, while the opposite side of the crystal is exposed to air at ambient pressure. The crystal is held in place between the two halves of the flow cell by two rubber O-rings. These O-rings are sufficiently soft to allow the crystal to vibrate freely.

Figure 3:
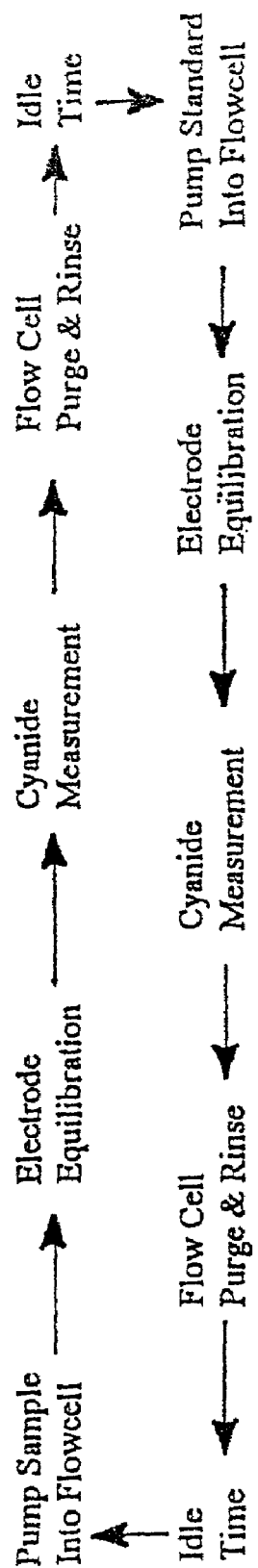
FIG. 3 illustrates the analysis/calibration protocol of the present invention.

The procedures for determination of cyanide in aqueous samples are straightforward, but must be performed in a regimented fashion in order to achieve adequate calibration and analytical measurements. FIG. 3 shows a typical sampling protocol for the cyanide detection system. In a laboratory prototype of the present invention, the aqueous solutions are introduced into the system by a peristaltic pump, which loads and removes the solutions to and from the flow cell. Solutions composed of cyanide standards or samples of unknown CN$^-$ concentration are introduced into the flow cell for a short rinse and equilibrium period (e.g., 2 minutes). This is followed by an analytical measurement time of two or more minutes at a flow rate of approximately 0.15 mL/min. The flow cell is then purged and rinsed in preparation for the next cycle of cyanide measurement. The oscillating frequency of the crystal can be measured in continuous or pulsed mode. Increased reaction time (residence time within the flow cell) provides increased method sensitivity.

As FIG. 3 indicates, the use of appropriate standard solution is required for the quantitative analysis of aqueous samples. In the quantitative mode it is standard procedure to alternate analytical standards and sample solution throughout the analysis period. However, semi-quantitative cyanide measurements can be made without the use of standards, using the Sauerbrey equation in conjunction with reaction efficiency data.

There are some conditions that may limit or impede detector operation: high turbidity (suspended solids) within the sample; high dissolved gases that might exsolve and adhere to the quartz surface (thus changing its vibrational characteristics); having a sample with viscosity that is markedly different than that of the cyanide standards; competition for the gold coating, etc. In some applications there may be some circuitry-related issues, such as the effect of strong emf fields. The effect of temperature on quartz crystal microbalance operation can be compensated for by establishing the standardization curve with standards that are the same temperature as the samples.

The foregoing description of the invention has been presented for purposes of illustration and description. It is not intended to be exhaustive or to limit the invention to the precise form disclosed, and obviously many modifications and variations are possible in light of the above teaching.

The embodiments described explain the principles of the invention and practical application and enable others skilled in the art to utilize the invention in various embodiments and with various modifications as are suited to the particular use contemplated. It is intended that the scope of the invention be defined by the claims appended hereto.

We claim:

1. A method for the real-time measurement of aqueous cyanide, comprising:
    providing a cyanide laden water test specimen in a flow cell, said flow cell adapted to contain a gold-plated piezoelectric crystal having a surface in fluid communication with said test specimen;
    providing a controller to control the oscillation frequency of the piezoelectric crystal;
    determining the cyanide concentration within said test specimen by measuring a change in said crystal oscillation frequency caused by a chemical reaction between free cyanide and the gold-plated piezoelectric crystal.

2. The method of claim 1 further comprising providing at least one known standard cyanide concentration for calibrating the piezoelectric oscillation frequency to the known standard concentration of cyanide.

3. The method of claim 1 further comprising preconditioning said test specimen to remove impurities by filtering said cyanide laden test specimen.

4. The method of claim 1 wherein a portion of said piezoelectric crystal surface is coated with fluorinated spray coating to prolong operation lifetime of said crystal.

5. The method of claim 1 further comprising collecting the test specimen to recover gold after said cyanide concentration of said test specimen has been determined.

6. The method of claim 1 further comprising purging and rinsing said flow cell after said cyanide concentration has been determined.

7. The method of claim 1 further comprising agitating said test specimen within said flow cell to promote continued mixing within said test specimen.

8. The method of claim 7 wherein the agitating is by ultrasonic vibration.

9. The method of claim 7 wherein the agitating is by a micro-stirrer.

10. The method of claim 1 further comprising displaying and recording in real-time said measured cyanide concentration.

11. A method for the continuous, real-time measurement of aqueous cyanide, comprising:
    providing a cyanide laden water test specimen in a flow cell;
    providing a flow cell stack comprising a plurality of flow cells, each flow cell adapted to contain a gold-plated piezoelectric crystal having opposite first and second surfaces, said first surface being in contact with the test specimen and said second surface being exposed to an ambient atmosphere;
    controlling the frequency of vibration of each piezoelectric crystal;
    measuring changes in the frequency of vibration of the piezoelectric crystal, said changes resulting from a change of mass of said crystal caused by the reaction of the gold on the crystal with cyanide in the test specimen.

12. The method of claim 11 further comprising at least one known standard cyanide concentration for calibrating the piezoelectric oscillation frequency to the known standard concentration of cyanide.

13. The method of claim 11 further comprising preconditioning said test specimen to remove impurities by filtering said cyanide laden test specimen.

14. The method of claim 11 wherein a portion of said piezoelectric crystal surface is coated with fluorinated spray coating to prolong operation lifetime of said crystal.

15. The method of claim 11 further comprising collecting the test specimens to recover gold after said cyanide concentrations of said test specimens have been determined.

16. The method of claim 11 further comprising purging and rinsing said flow cells after said cyanide concentration has been determined.

17. The method of claim 11 further comprising agitating said test specimen within said flow cell to promote continued mixing within said test specimen.

18. The method of claim 17 wherein the agitating is by ultrasonic vibration.

19. The method of claim 17 wherein the agitating is by a micro-stirrer.

20. The method of claim 10 further comprising displaying and recording in real-time said measured cyanide concentration.

21. A continuous, real time cyanide concentration measurement system, comprising;
    at least one flow cell adapted to contain a gold-plated piezoelectric crystal, said crystal having first and second surfaces, said first surface configured to contact a test specimen within the at least one flow cell and said second surface configured to contact an ambient atmosphere;
    agitation means for promoting mixing the test specimen within the at least one flow cell;
    means for purging and rinsing said flow cell;
    a controller to control and measure changes in oscillation frequency of said crystal caused by a chemical reaction between free cyanide within the test specimen and the gold-plated piezoelectric crystal.

22. The system of claim 21 further comprising at least one known standard cyanide concentration for calibrating the piezoelectric oscillation frequency to the known concentration of cyanide.

23. The system of claim 21 further comprising a filter to precondition the test specimen to remove impurities prior to the test specimen being contained in said flow cell.

24. The system of claim 23 wherein said filter is a semi-permeable membrane.

25. The system of claim 21 further comprising means for adjusting pH of said test specimen to a pH between 10 and 12.

26. The system of claim 21 wherein a portion of said first surface of said piezoelectric crystal is coated with a fluorinated spray coating to prolong operation lifetime of said crystal.

27. The system of claim 21 further comprising collection means for collecting test specimens to recover gold.

28. The system of claim 21 further comprising real-time display and recording means of displaying and recording said measured cyanide concentration.

29. The system of claim 21 further comprising dual piezoelectric oscillator circuits to allow simultaneous measurement of said changes in oscillation frequency of multiple piezoelectric crystals.

30. The system of claim 21 further comprising means for directing said test specimens to specific flow cells within a flow cell stack.

* * * * *